United States Patent
Chilekar et al.

(10) Patent No.: US 9,132,387 B2
(45) Date of Patent: Sep. 15, 2015

(54) PROCESS FOR WORKING-UP A REACTION MIXTURE COMPRISING POLYETHER POLYOL

(71) Applicants: Vinit Chilekar, Tervuren (BE); Hartwig Voss, Frankenthal (DE); Jelan Kuhn, Heidelberg (DE); Ann De Colvenaer, Wommelgem (BE); Andreas Brodhagen, Tiefenthal (DE)

(72) Inventors: Vinit Chilekar, Tervuren (BE); Hartwig Voss, Frankenthal (DE); Jelan Kuhn, Heidelberg (DE); Ann De Colvenaer, Wommelgem (BE); Andreas Brodhagen, Tiefenthal (DE)

(73) Assignee: BASF SE, Lugwigshafen (DE)

( * ) Notice: Subject to any disclaimer, the term of this patent is extended or adjusted under 35 U.S.C. 154(b) by 322 days.

(21) Appl. No.: 13/712,536

(22) Filed: Dec. 12, 2012

(65) Prior Publication Data
US 2013/0146537 A1  Jun. 13, 2013

Related U.S. Application Data

(60) Provisional application No. 61/569,813, filed on Dec. 13, 2011.

(51) Int. Cl.
*B01D 11/02* (2006.01)
*B01D 61/24* (2006.01)
(Continued)

(52) U.S. Cl.
CPC .......... *B01D 61/246* (2013.01); *B01D 11/0288* (2013.01); *B01D 11/0292* (2013.01); *B01D 11/0415* (2013.01); *B01D 61/243* (2013.01); *C07C 41/38* (2013.01)

(58) Field of Classification Search
CPC .............. B01D 11/02; B01D 11/0288; B01D 11/0292; B01D 2311/26; B01D 2311/2623; B01D 2311/2696; B01D 61/24; B01D 61/243; B01D 11/0415; B01D 61/246; C07C 41/34; C07C 41/38; C07C 41/44; C07C 45/80
USPC .................. 210/634, 638, 639, 644, 649–651; 568/613, 620, 621, 671, 672, 679, 699
See application file for complete search history.

(56) References Cited

U.S. PATENT DOCUMENTS 3,441,616 A * 4/1969 Pizzini et al. ................ 568/621
3,865,806 A * 2/1975 Knodel ........................ 536/120
(Continued)

FOREIGN PATENT DOCUMENTS

DE   100 54 462 A1   6/2002
EP   0 982 283 A2    3/2000
(Continued)

OTHER PUBLICATIONS

International Search Report issued Dec. 2, 2013 in PCT/EP2012/075411.

*Primary Examiner* — Joseph Drodge
(74) *Attorney, Agent, or Firm* — Oblon, McClelland, Maier & Neustadt, L.L.P.

(57) ABSTRACT

The invention relates to a process for working-up a reaction mixture (5) comprising polyetherol and dissolved alkali metal comprising catalyst, wherein at least alkali metal ions of the dissolved alkali metal comprising catalyst are partially or completely removed from the mixture by a membrane separation process, the process comprising following steps:
(a) feeding the reaction mixture (5) comprising polyetherol and dissolved alkali metal comprising catalyst into a first chamber (1) of a separation unit (3),
(b) feeding a solvent into a second chamber (7) of the separation unit (3), the first chamber (1) and the second chamber (7) being separated by a membrane (9),
(c) transporting at least the alkali metal ions of the alkali metal comprising catalyst from the first chamber (1) into the second chamber by passing through the membrane (9).

16 Claims, 2 Drawing Sheets

(51) Int. Cl.
*C07C 41/38* (2006.01)
*B01D 11/04* (2006.01)

(56) References Cited

U.S. PATENT DOCUMENTS

| | | | | |
|---|---|---|---|---|
| 4,946,939 | A * | 8/1990 | Murphy et al. | 528/421 |
| 5,773,667 | A * | 6/1998 | Bahrmann et al. | 568/454 |
| 5,817,884 | A * | 10/1998 | Bahrmann | 568/454 |
| 8,461,285 | B2 * | 6/2013 | Ahmadnian et al. | 528/76 |
| 2003/0028044 | A1 * | 2/2003 | Buchanan et al. | 558/277 |
| 2003/0168404 | A1 * | 9/2003 | Mika et al. | 210/639 |
| 2004/0073069 | A1 | 4/2004 | Heider et al. | |
| 2004/0211729 | A1 | 10/2004 | Sunkara et al. | |
| 2004/0267056 | A1 | 12/2004 | Mellado et al. | |
| 2005/0258100 | A1 * | 11/2005 | Lightfoot | 210/641 |
| 2006/0065600 | A1 | 3/2006 | Sunkara et al. | |
| 2012/0178834 | A1 * | 7/2012 | Linder et al. | 521/27 |
| 2013/0079558 | A1 * | 3/2013 | Lousenberg | 564/296 |
| 2014/0303405 | A1 * | 10/2014 | Osborne et al. | 568/679 |

FOREIGN PATENT DOCUMENTS

| | | |
|---|---|---|
| EP | 0 982 283 A3 | 3/2000 |
| EP | 1 493 769 A1 | 1/2005 |
| GB | 142899 | 5/1920 |
| WO | WO 90/15659 A1 | 12/1990 |
| WO | WO 01/36514 A1 | 5/2001 |

* cited by examiner

PROCESS FOR WORKING-UP A REACTION MIXTURE COMPRISING POLYETHER POLYOL

CROSS-REFERENCE TO RELATED APPLICATIONS

This application is based upon and claims the benefit of priority to U.S. Provisional Application No. 61/569,813 filed on Dec. 13, 2011.

The invention relates to a process for work-up of a reaction mixture comprising polyether polyol (Polyetherol) and dissolved alkali metal comprising catalyst, wherein at least alkali metal ions of the dissolved alkali metal comprising catalyst are partially or completely removed from the mixture.

Polyetherols are an important raw material in the production of polyurethanes. Further, polyetherols are also used as tensides. The production of polyetherols generally is carried out by a catalytic addition of alkylene oxides, particularly propylene oxide and/or ethylene oxide and/or butylene oxide to H-functional starter substances. As a catalyst generally alkali metal hydroxides or salts are used. Of major practical relevance is potassium hydroxide.

In the reaction firstly an alcohol (also called as starter compound) reacts with a base, for example potassium hydroxide, forming the corresponding alcoholate. During this reaction, water is also formed. The water is either partially or completely removed, for example by distillation or stripping or flashing or left within the alcoholate for further reaction, and the alcoholate with or without water further reacts with alkylene oxide, for example propylene oxide, ethylene oxide or a mixture of both. The resulting products are mixtures of homologues of different chain lengths.

A continuous process for the production of polyetherols is described for example in GB 142 899. This process is based on potassium hydroxide catalysts and as reactors separate vertically cascaded bubble columns are used. In such a vertically cascaded bubble column reactor propylene oxide, potassium hydroxide and an alcohol starter are fed to the bottom and the product along with unreacted propylene oxide gas is withdrawn at the top of the column. Following the column, the unreacted propylene oxide is separated off in a condenser and recycled to the column. In a final step the reaction product is neutralized by adding an acid.

Further processes for forming polyetherols are described in WO-A 01/36514 and DE-B 100 54 462. According to the disclosure of these documents, the catalyst is neutralized with an acid, for example acetic acid or citric acid and remains in the product. In an alternative, the salt is precipitated or crystallized and removed. The removal of the salt generally is carried out by a filtration process. However, removing the catalyst by firstly neutralizing with an acid and removing the formed salt by filtration has the disadvantage that there is a product loss in the filtered salt of the alkali metal catalyst. The viscosity of polyether polyol hinders better drying of the filter cake; hence the product loss cannot be avoided. To have a better drying of the filter cake, larger crystals of the salt are necessary, which requires a long crystallization time. This limits the production capacity of the process. The disposal of the filter cake containing polyether polyol adds up to the waste disposal costs.

Therefore, it is an object of the invention to provide a process for working-up a reaction mixture comprising polyetherol and dissolved alkali metal comprising catalyst which does not exhibit the disadvantages of the known processes.

This object is achieved by a process for working-up a reaction mixture comprising polyetherol and dissolved alkali metal comprising catalyst, wherein at least alkali metal ions of the dissolved alkali metal comprising catalyst are removed from the mixture by a membrane separation process, the process comprising following steps:

(a) feeding the reaction mixture comprising polyetherol and dissolved alkali metal comprising catalyst into a first chamber of a separation unit,
(b) feeding a solvent into a second chamber of the separation unit, the first chamber and the second chamber being separated by a membrane,
(c) transporting at least the alkali metal ions of the alkali metal comprising catalyst from the first chamber into the second chamber by passing through the membrane.

In contrast to the known processes, in which the polyetherol is neutralized and filtered, which involves solid handling, solid waste disposal and product loss in solid waste, in the inventive process there is no solid waste produced, which reduces the waste disposal costs. Further, there is no loss of polyetherol during the membrane separation whereas in a filtration process also polyetherol is lost. Finally, by using a membrane for removing the alkali metal ions from the polyetherol, a product can be achieved which contains alkali metal ions comparable to the polyetherol which is worked-up in a process as known from the art.

The reaction mixture comprising polyetherol and dissolved alkali metal comprising catalyst originates from a process to produce polyetherols. The process to produce polyether polyol could be a semi-batch process or a continuous process. In a Semi-batch process, the alkylene oxide is added in one sequence or multiple sequences to a mixture of H-functional starter containing alkali metal catalyst as per the required structure of the polyetherol. In a continuous process, the reaction generally is performed in a reactor which is designed as a bubble column or a continuous stirred tank reactor (CSTR) or a cascade of CSTRs or a Plug flow reactor or a combination of all of the above mentioned reactors. In case of a bubble column an alcohol and a starter or an alkoxylated precursor is fed. Further, an alkylene oxide is fed into the reactor at the bottom of the bubble column such that the alkylene oxide rises in the alcoholate. The alkylene oxide reacts with the alcoholate or a secondary product being formed by the reaction of alcoholate with alkylene oxide to get the polyetherol. Finally, the reaction product is discharged from the reactor and worked-up.

The reaction in the bubble column is carried out in the presence of a catalyst. The catalyst, which is used for the reaction, generally is a base. The base is preferably elected from hydroxides of alkali metals. Particularly preferable is potassium hydroxide or sodium hydroxide. Therefore, the alkali metal comprising catalyst, which is in the reaction mixture and has to be removed, is in a preferred embodiment an alkali metal hydroxide.

The alcohol starter which is used is a monovalent or polyvalent alcohol, particularly a fatty alcohol, oxoalcohol and/or secondary alcohol or a mixture of alcohols. Particularly preferred are low molecular tri-functional alcohols. Particularly preferred as an alcohol are glycerine, propylene glycol, ethylene glycol, trimethylol propane, sorbitol, and/or saccharide. Besides alcohols, further amines like ethylene diamine, triethanol amine or toluene diamine, heptane, alkyl phenol, or natural or synthetic fatty alcohols, fatty amines and hydrogenated amines, fatty amides, fatty acids, sorbitane esters, monoglycerides or monoesterides can be used. Particularly preferred as alcohols are glycerine, propylene glycols, dipropylene glycols and/or trimethylol propane.

The alkylene oxide which is used for the production of polyetherol is preferably ethylene oxide or propylene oxide. Also mixtures of ethylene oxide and propylene oxide can be used. Further, it is possible to use different alkylene oxides simultaneously and/or sequentially, wherein in case the alkylene oxides are fed sequentially, at least two reactors or compartments are provided and to which the alkylene oxides are fed.

Besides ethylene oxide and propylene oxide further butylene oxide can be used. If butylene oxide is used, generally mixtures with ethylene or propylene oxide are used.

To keep the gas phase concentration of alkylene oxide below the gas phase decomposition limit, it is preferred to feed the alkylene oxide into the reactor in form of the mixture comprising alkylene oxide and an inert gas. The inert gas can be for example nitrogen. Besides nitrogen also other gases that are inert to the reaction can be used.

The gaseous component present in the reaction mixture could be separated before or even after the reaction mixture is worked-up as per the present invention. To remove the gaseous components, each process as known by a skilled person can be used.

In WO-A 1990/015659, an electric field was applied to achieve the separation of catalyst ions from polyetherpolyols as per the electrodialysis technique. In the present invention there is no use of any electric field to enhance the separation of ions.

In the present invention, the reaction mixture is fed into the first chamber of the separating unit to remove the alkali metal ions of the alkali metal comprising catalyst by a membrane separation process. In a preferred embodiment, the membrane separation is operated using Donnan dialysis. In an alternative embodiment the membrane separation could also be done using nanofiltration.

To achieve a selective separation of the alkali metal ions via the membrane of the membrane separation process, it is required that the membrane is an ion exchange membrane, preferably a cation exchange membrane. Suitable membranes which can be used as cation exchange membranes are for example membranes as used in polymer membrane electrolyte fuel cells, such as Nafion®, sulfonated poly(etheretherketone) (SPEEK), blends and copolymers of SPEEK, such as blend with polysulfone, sulfonated polyaryletherketone, which can be arranged in hollow fiber, flat sheet or tubular configuration.

For carrying out the separation process it is necessary that solvent containing an acid is fed into the second chamber of the separation unit. The protons for the acid will diffuse through the cation conducting membrane due to the gradient in concentration. This will result in a netto positive charge in the first chamber, which leads to diffusion of alkali cations from the first to the second chamber, resulting in a continuous cation exchange over the membrane. The concentration of alkali metal ions in the solvent has to be smaller than the concentration of alkali metal ions in the reaction mixture to have a concentration gradient from the first chamber to the second chamber. Therefore, a fresh or recycled acid stream must be fed to the second chamber. The reaction mixture in the first chamber and the acid in the second chamber can flow in counter-current, co-current, cross-flow or in any combination thereof.

The solvent which is fed into the second chamber is preferably selected from the group consisting of water, acid, and an organic solvent that does not swell the membrane or mixtures thereof. Suitable acids are for example phosphoric acid, carbonic acid, hydrochloric acid, nitric acid or sulphuric acid and other organic acids, preferably inorganic acids.

To perform the membrane separation process, at least one separating unit is used. The separating unit comprises at least one membrane module, preferably more than one membrane module. The membrane modules which are comprised in the separating unit are preferably selected from hollow fiber modules, flat sheet modules or tubular modules.

Hollow Fiber Modules and Spiral Wound modules have a much higher specific surface area and are therefore, generally, more cost effective. However, Spiral Wound modules can not be used in this case, as these can not have two feeds in counter or co-current.

To achieve a sufficient separating efficiency, it is preferred to use at least two membrane modules, wherein the membrane modules can be connected in parallel or in series. If the membrane modules are connected in series, it is further possible that the reaction mixture flows through the membrane modules one after another, whereas the solvent is fed into the second chamber of each membrane module and removed after flowing through the membrane module. Such a conduction of the flow has the advantage that into each membrane module a solvent is fed which is free from alkali metal ions. This leads to a better separation performance in the respective modules.

As a membrane, which separates the first chamber and the second chamber of the separation unit, any type of membrane which is known to a skilled person can be used.

For the present invention the preferred membrane separation process is Donnan Dialysis, for which only polymer membranes can be used. In a preferred embodiment a polymer membrane comprising a support is used. The membrane support can be any membrane support known to a person skilled in the art, for example Teflon® or Ceramic support or any other typical support which improves the thermal stability of the membrane. Ceramic membranes are generally more chemically and thermally stable, but have not been developed for this application until now.

To achieve a sufficient separation efficiency, it is preferred to carry out the separation process at a temperature in the range from 50 to 300° C., preferably at a temperature in the range from 50 to 200° C. and particularly preferred at a temperature in the range from 60 to 150° C.

The pressure at which the separation process is carried out is preferably in the range from 1 to 4 bar in both chambers. The pressure difference between the chambers is preferably in the range of 0.01 to 1 bar, particularly preferred in the range from 0.01 to 0.5 bar. The current Hollow Fiber Modules are only suited for low pressure differences of up to 0.3 bar. Therefore, if Hollow Fiber Modules are used, the pressure gradient between the chambers separated by the membrane should not exceed the admissible pressure difference of the used membrane. Due to the low pressure difference counter current operation could be less suitable than co current.

To avoid fouling of the membranes in the first chamber and further to get a sufficient amount of the reaction mixture through the first chamber of the separation unit, it is preferred when the reaction mixture comprises a solvent to improve the ionic mobility in the reaction mixture. The solvent thereby is preferably selected from the group consisting of water, isopropanol, ethylene glycol, propylene glycol, methanol, ethanol, acetone and mixtures thereof. Preferably solvents are used which do not swell the membrane too much.

The polyetherols produced are used for example for polyurethane applications, particularly for the production of polyurethanes.

The invention is described in detail herein below with the reference to a drawing.

In the drawing:

FIG. 1 shows the inventive process in a first embodiment.

Figure 1:
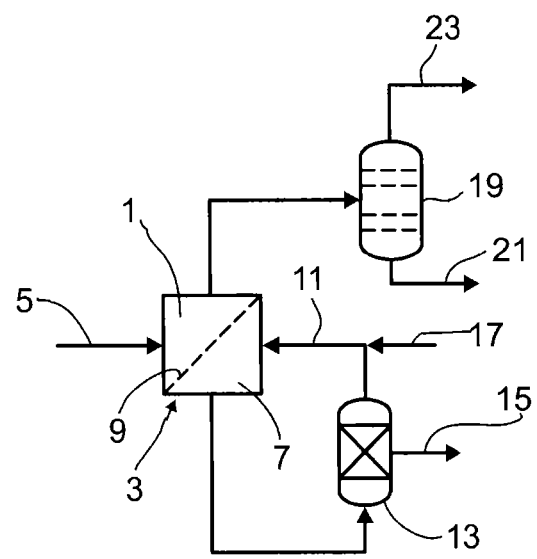
FIG. 1 shows a schematic process flow chart of the inventive process in a first embodiment.

Into a first chamber 1 of a separation unit 3 a reaction mixture 5, comprising polyetherol and dissolved alkali metal comprising catalyst is fed.

The reaction mixture 5 originates from a process of producing polyetherol in which an alcohol starter reacts in the presence of an alkali metal catalyst, forming an alcoholate and water. The water is afterwards removed and the alcoholate is fed into a reactor, preferably a bubble column. Into the bubble column also gaseous alkylene oxide is fed. In presence of the alkali metal comprising catalyst the alcoholate and the alkylene oxide react, forming polyetherol. The resulting reaction mixture comprises polyetherol and alkali metal catalyst, wherein the amount of alkali metal catalyst is in the range from 0.0001 to 5 wt-%, preferably in the range from 0.0005 to 1 wt-%.

This reaction mixture is then fed as stream 5 into the first chamber 1 of the separation unit 3.

The separation unit 3 further comprises a second chamber 7, wherein the first chamber 1 and the second chamber 7 are separated by a membrane 9.

The separation unit, which is schematically shown in FIG. 1, is for example a membrane separation unit which preferably comprises membrane modules such as hollow fiber modules, spiral wound membrane modules, flat modules, or tubular modules.

The membrane 9 which separates the first chamber 1 and the second chamber 7 is preferably a cation exchange membrane. Suitable membranes are for example membranes as used in polymer membrane electrolyte fuel cells, such as Nation, sulfonated poly(etheretherketone) (SPEEK), blends and copolymers of SPEEK, such as blends with polysulfone, sulfonated polyaryletherketone, which can be arranged in hollow fiber, flat sheet or tubular configuration.

In the separation unit 3, alkali metal ions are removed from the reaction mixture by diffusion over the membrane 9. To remove the alkali metal ions from the reaction mixture 5, a solvent 11 flows through the second chamber 7. The solvent 11 for example is an aqueous acidic solution, which can contain an organic solvent additive. Suitable acids are for example phosphoric acid, carbonic acid, hydrochloric acid, nitric acid or sulfuric acid.

After flowing through the second chamber, the solvent 11 comprises alkali metal ions. The solvent 11 comprising alkali metal ions is fed into a separation unit 13, in which the alkali metal ions are removed from the solvent. If the solvent 11 is an acid, the alkali metal ions form salts with the anions of the acid. In the separation unit 13 these salts are removed. The removal of the salts can be carried out for example by adsorption or liquid-liquid extraction or any other known separation process to a skilled person.

The salts are removed via a discharge line 15.

After removing the salts comprising the alkali metal ions, the solvent is recycled into the second chamber 7 of the separation unit 3. To compensate losses of solvent which can be removed via the discharge line 15, a feeding line 17 is provided through which additional solvents can be fed into the process.

After flowing through the first chamber 1, the reaction mixture from which the alkali metal ions are removed, is fed into a stripper 19. In the stripper, polyetherol and solvent of the reaction mixture are separated. Via a bottom of the stripper 19 polyetherol is removed as a product via product discharge line 21 and the solvent, for example water, is removed via a solvent discharge line 23 at the top of the stripper 19. Separating polyetherol and solvent for example is carried out by stripping column.

Figure 2:
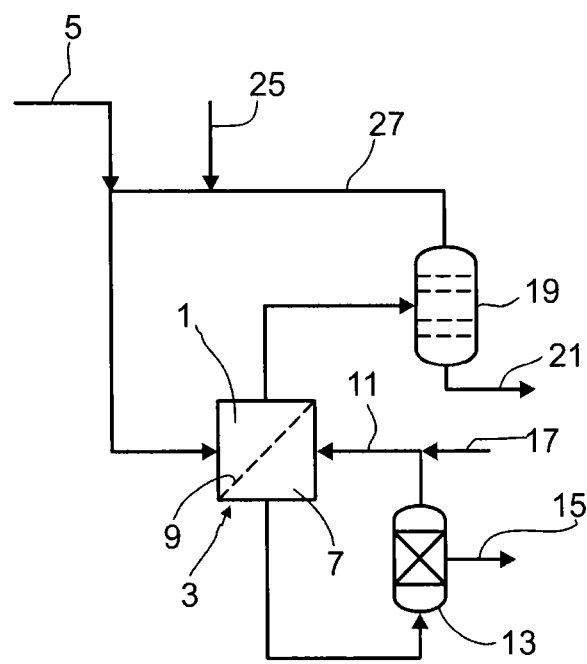
FIG. 2 shows a schematic process flow chart of the inventive process in a second embodiment.

FIG. 2 shows an inventive process in a second embodiment.

The embodiment of FIG. 2 differs from FIG. 1 in the fact that the solvent which is discharged at the top of the stripper 19 is recycled into the feeding line of the reaction mixture 5. Further, to compensate losses of solvents in the reaction mixture, additional solvent can be fed into the process. According to FIG. 2, the solvent is fed via a feeding line 25 into the recycling line 27 of the solvent which is drawn off the top of the stripper 19. According to the process of FIG. 2 all streams are recycled and only the product is removed via the product discharge line 21 and the catalyst is removed via the discharge line 15.

LIST OF REFERENCE NUMERALS

1 first chamber
3 separation unit
5 reaction mixture
7 second chamber
9 membrane
11 solvent
13 separation unit
15 discharge unit
17 feeding line
19 stripper
21 product discharge line
23 solvent discharge line
25 feeding line
27 recycling line

The invention claimed is:

1. A process for working-up a reaction mixture, the process comprising:
    (a) feeding a reaction mixture comprising a polyetherol and a dissolved alkali metal comprising catalyst into a first chamber of a separation unit;
    (b) feeding a solvent into a second chamber of the separation unit, the first chamber and the second chamber being separated by a membrane; and
    (c) partially or completely transporting at least alkali metal ions of the alkali metal comprising catalyst from the first chamber into the second chamber by passing through the membrane.

2. The process according to claim 1, wherein the alkali metal comprising catalyst is an alkali metal hydroxide.

3. The process according to claim 1, wherein membrane separation occurs by a Donnan dialysis process.

4. The process according to claim 1, wherein the reaction mixture is a product stream of a reaction for producing the polyetherol by reacting an alcoholate with alkylene oxide, the alcoholate being formed by reaction of an alcohol with the catalyst.

5. The process according to claim 1, wherein the alkali metal comprising catalyst is selected from the group consisting of sodium hydroxide and potassium hydroxide.

6. The process according to claim 1, wherein the membrane is a cation exchange membrane.

7. The process according to claim 1, wherein the solvent is an aqueous acidic solution optionally comprising at least one selected from the group consisting of an alcohol, an ether, a ketone and a mixture thereof.

8. The process according to claim 7, wherein an acid of the aqueous acidic solution is selected from the group comprising phosphoric acid, carbonic acid, hydrochloric acid, nitric acid, sulfuric acid, and a mixture thereof.

9. The process according to claim 1, wherein the separation unit comprises at least one membrane module selected from the group consisting of a hollow fiber module, a membrane module, a flat sheet module, and a module with a tubular configuration.

10. The process according to claim 9, wherein at least two membrane modules are connected in parallel or in series.

11. The process according to claim 1, wherein the membrane is a polymer membrane.

12. The process according to claim 11, wherein the polymer membrane comprises a support.

13. The process according to claim 1, wherein the separation occurs at a temperature in the range from 50 to 300° C.

14. The process according to claim 1, wherein the reaction mixture further comprises a solvent to improve ionic mobility in the reaction mixture.

15. The process according to claim 14, wherein the solvent to improve the ionic mobility in the reaction mixture is selected from the group consisting of water, isopropanol, ethylene glycol, propylene glycol, methanol, ethanol, acetone and a mixture thereof.

16. The process according to claim 1, which produces at least one polyetherol adapted to polyurethane applications.

* * * * *